United States Patent [19]
Schulz

[11] Patent Number: 5,364,362
[45] Date of Patent: Nov. 15, 1994

[54] FRONT SYRINGE ATTACHMENT FOR HYPODERMIC SYRINGES FOR SUBCUTANEOUS INJECTION IN VETERINARY MEDICINE

[75] Inventor: Dieter Schulz, Mühlheim, Germany

[73] Assignee: Henke-Sass, Wolf GmbH, Tuttlingen, Germany

[21] Appl. No.: 18,698

[22] Filed: Feb. 17, 1993

[30] Foreign Application Priority Data

Feb. 19, 1992 [DE] Germany ............... 4205036

[51] Int. Cl.⁵ .............................................. A61M 5/00
[52] U.S. Cl. ............................. 604/115; 604/192; 604/198
[58] Field of Search ............... 604/115, 116, 117, 110, 604/187, 218, 198, 197, 265, 192, 162; 128/919

[56] References Cited

U.S. PATENT DOCUMENTS

| | | |
|---|---|---|
| 4,067,334 | 1/1978 | Haller . |
| 4,507,118 | 3/1985 | Dent ................... 604/198 |
| 4,642,099 | 2/1987 | Phillips et al. ........... 604/136 |
| 4,666,436 | 5/1987 | McDonald et al. ......... 604/198 |
| 4,850,996 | 7/1989 | Cree ................... 604/198 |
| 4,894,055 | 1/1990 | Sudnak ................. 604/198 |
| 4,911,693 | 3/1990 | Paris ................... 604/192 |
| 4,923,447 | 5/1990 | Morgan ................ 604/198 |
| 4,936,830 | 6/1990 | Verlier ................ 604/110 |
| 5,026,353 | 6/1991 | Bartman ............... 604/192 |
| 5,256,152 | 10/1993 | Marks ................. 604/198 |

FOREIGN PATENT DOCUMENTS 3012851 10/1981 Germany .
4019656 3/1991 Germany .

*Primary Examiner*—C. Fred Rosenbaum
*Assistant Examiner*—V. Alexander
*Attorney, Agent, or Firm*—McAulay Fisher Nissen Goldberg & Kiel

[57] ABSTRACT

A front syringe attachment is provided for mounting on a syringe cylinder of hypodermic syringes for subcutaneous injection, particularly for use in veterinary medicine, which substantially includes a first hollow-cylindrical barrel and a second hollow-cylindrical barrel of smaller diameter which is arranged in the latter in a telescoping manner, wherein the end of the first barrel facing the syringe cylinder is fastened to the syringe cylinder and the end of the second barrel facing the syringe cylinder can be pushed into the first barrel against a spring arranged in the first barrel, and the ends of the two barrels on the injecting side have a step-like or stair-like construction, wherein the end of the second barrel on the injecting side projects beyond the end of the first barrel on the injecting side in the rest position and completely covers the hypodermic needle.

5 Claims, 2 Drawing Sheets

1

FRONT SYRINGE ATTACHMENT FOR HYPODERMIC SYRINGES FOR SUBCUTANEOUS INJECTION IN VETERINARY MEDICINE

BACKGROUND OF THE INVENTION a) Field of the Invention

The invention is directed to a front syringe attachment for mounting on syringe cylinders of hypodermic syringes for subcutaneous injection, particularly for use in veterinary medicine.

b) Related Art

Such hypodermic syringes for use in veterinary medicine frequently take the form of inoculation guns and are used by veterinarians for mass inoculation of animals. These inoculation guns are provided with a motor-driven injection plunger and the syringe cylinder is automatically filled after every inoculation process by feeding the inoculant from an external supply container connected with the inoculation gun via a tube so that the individual inoculations can be carried out relatively quickly one after the other (DE-OS-40 19 656).

In the case of cattle intended for slaughter, a special inoculation technique is used so as not to damage the quality of the flesh for later consumption by injected medications, namely subcutaneous injection, i.e., the inoculant is injected between the skin H and layers of muscle M located below the skin, whereby the veterinarian forms a fold of skin, the so-called "subcutaneous tent", by pinching the layer of skin with his fingers before inserting the needle. The inoculation gun with the needle is then placed against this "subcutaneous tent", the needle is inserted into the fold of skin, and the inoculant is injected.

This injection technique, however, requires that the veterinarian perform the inoculation with both hands, i.e., he does not have a free hand for holding the animal to be inoculated, another person is needed for this.

A hypodermic syringe of the type mentioned above is known from U.S. Pat. No. 4,067,334, in which its positioning on the animal's body is facilitated by an angled, slotted attachment.

DE-OS 30 12 851 discloses a device for facilitating the subcutaneous injection of insulin in which a diagonally slit tube encloses the hypodermic needle and tenses the skin when pressed against the skin.

OBJECT AND SUMMARY OF THE INVENTION

A primary object of the present invention is to provide a front syringe attachment for mounting on syringe cylinders, particularly of syringes for use in veterinary medicine, which front syringe attachment forms the "subcutaneous tent" when the syringe is placed against the skin H of the animal to be inoculated and ensures that the needle accurately penetrates below this "subcutaneous tent" and accordingly brings about the advantage that the veterinarian operating the inoculation gun can inject animals subcutaneously with one hand.

This object is met in that a front syringe attachment for mounting on syringe cylinders of hypodermic syringes for subcutaneous medicine, particularly in veterinary medicine substantially includes a first hollow-cylindrical tube or barrel and a second hollow-cylindrical barrel of smaller diameter which is arranged in the first barrel in a telescoping manner, wherein the first barrel is fastened at the syringe cylinder by its end facing the latter and the second barrel can be pushed into the outer barrel by its end facing the syringe cylinder against a spring arranged in the outer barrel, and in that the ends of the two barrels on the injecting side have a step-like or stair-like construction, wherein the end of the second barrel on the injecting side projects beyond the end of the first barrel on the injecting side in the rest position and entirely covers the hypodermic needle.

This construction of the front syringe attachment ensures that when the inoculation gun is applied in the axial direction of the hypodermic needle a "subcutaneous tent" is first formed on the skin of the animal to be inoculated before the hypodermic needle has penetrated the body of the animal. This penetration is effected only when the second hollow-cylindrical barrel is pushed into the first barrel against the force of a spring due to the increase in pressure on the inoculation gun in the longitudinal direction of the hypodermic needle and the hypodermic needle is accordingly released for penetrating into the "subcutaneous tent".

The spring is advantageously constructed as a cylindrical helical spring.

In a further advantageous construction of the invention a groove extending in the longitudinal direction of the barrel is cut into the outer wall opposite the beveled end of the second barrel and a guide pin provided in the first barrel projects into this groove.

This construction prevents a relative rotation of the first and second barrels so that the ends of the two barrels on the injecting side which are beveled in a step-like or stair-like manner correspond to one another in the pushed in state.

For a better understanding of the present invention, reference is made to the following description and accompanying drawings while the scope of the invention will be pointed out in the appended claims.

DESCRIPTION OF THE PREFERRED EMBODIMENT

Figure 1:
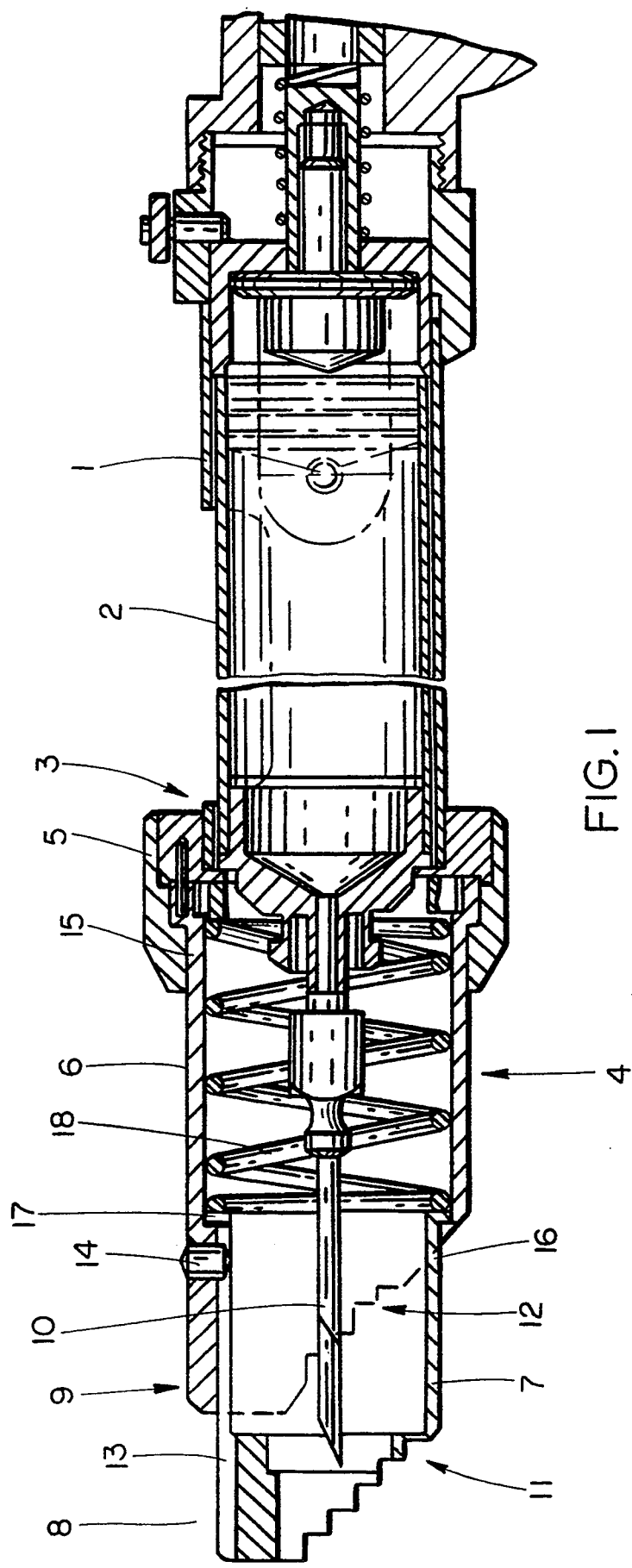
FIG. 1 shows a section through the front syringe attachment and the syringe cylinder of an inoculation gun, not shown, in the rest position.

A syringe cylinder 2 of glass or plastic is held on an inoculation gun, not shown in the drawing, in a socket or holder 1 arranged at the latter, a front syringe attachment 4 being fastened at its front end 3 by means of a coupling nut 5.

The front syringe attachment 4 comprises a first, outer hollow-cylindrical barrel 6 and a second, inner hollow-cylindrical barrel 7 which is arranged in the latter so as to be longitudinally displaceable and whose end 8 on the injecting side projects beyond the end 9 of the first barrel 6 until it completely covers the hypodermic needle 10 enclosed by the front syringe attachment 4.

The two ends 8 and 9 of the first and second barrels 6 and 7, respectively, on the injecting side are diagonally beveled at a determined angle relative to their diametrical planes and have step-like or stair-like constructions 11 and 12, respectively, which coincide when the second barrel 7 is pushed in.

To ensure this overlapping, which is necessary for carrying out faultless inoculations, i.e., to prevent a turning of the second barrel 7 in the first barrel 6, the second barrel 7 has a groove 13 which is cut in on its outer wall in the longitudinal direction. A guide pin 14 which is provided in the first barrel 6 projects into the groove 13.

The inner diameter of the first barrel 6 is smaller in the region of the step-like or stair-like construction 12 than in the inner portion adjoining it up to its end 15 facing the syringe cylinder.

The second barrel 7 projects into this widened diametrical area of the first barrel 6 with a collar 17 provided at its end 16 facing the syringe cylinder 2.

A helical spring 18 which is installed in the interior of the first barrel 6 having the greater inner diameter contacts this collar.

Figure 2:
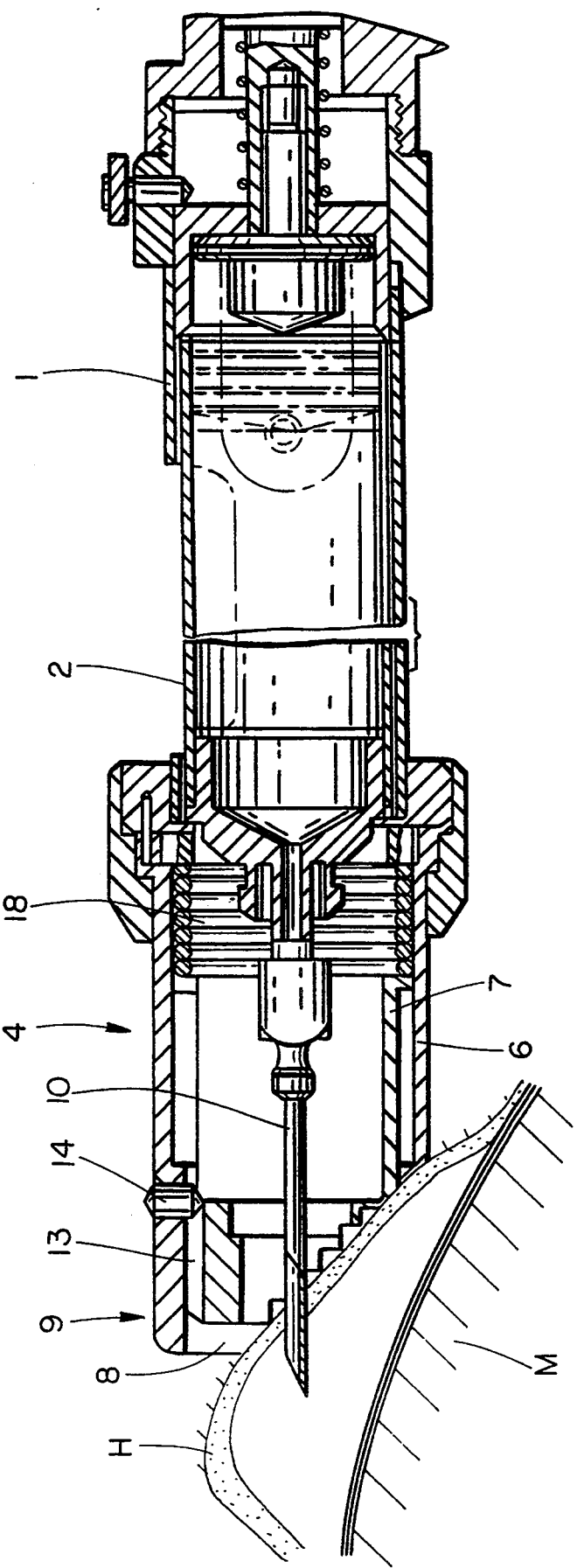
FIG. 2 shows a section according to FIG. 1, but in the inoculating position.

To carry out the inoculation, the inoculation gun outfitted with the front syringe attachment 4 described above is applied to the skin H of the animal to be inoculated in the longitudinal direction of the hypodermic needle 10 by the veterinarian. A fold of skin, the so-called "subcutaneous tent", is formed, as shown in FIG. 2, when the second barrel of the front syringe attachment 4 is first pressed against the animal by its end 8 on the injecting side having the step-like or stair-like construction 11. When the veterinarian increases the pressure of the inoculation gun on the skin H of the animal to be inoculated, the second barrel 7 of the front syringe attachment 4 begins to slide into the interior of the first barrel 8 of the front syringe attachment 4 against the pressure of the helical spring 18, wherein the "subcutaneous tent" is further developed. The hypodermic needle 10 which is freed when the second barrel 7 is pushed in then penetrates into this "subcutaneous tent" and the veterinarian can inject the inoculant.

The veterinarian can perform inoculations with one hand due to this front syringe attachment according to the invention, i.e., he can use his other hand or arm for calming or holding the animal to be inoculated.

While the foregoing description and drawings represent the preferred embodiments of the present invention, it will be obvious to those skilled in the art that various changes and modifications may be made therein without departing from the true spirit and scope of the present invention.

What is claimed is:

1. In a front attachment for mounting on a syringe cylinder of a hypodermic syringe for subcutaneous injection, the improvement comprising:
   a first hollow-cylindrical barrel having a first diameter and a first end, said first end being removably connected to the syringe cylinder;
   a second hollow-cylindrical barrel having a diameter smaller than said first diameter, said first barrel in telescopic relation with said second barrel, said second barrel having a second end, said second end facing the syringe cylinder, said second barrel being retractable from a rest position within said first barrel; and
   spring means in said first barrel, said first and second barrels each having an opposite end on an injecting side, said opposite ends having a steplike construction, wherein said opposite end of said second barrel projects beyond said opposite end of said first barrel and completely covers a hypodermic needle while occupying said rest position.

2. The front syringe attachment according to claim 1, wherein said spring means is constructed as a cylindrical helical spring.

3. The front syringe attachment according to claim 1 further comprising a guide pin, said guide pin in said first barrel and projecting into a groove in an outer wall of said second barrel.

4. A front syringe attachment comprising;
   a first hollow barrel mountable on a cylinder syringe;
   a second hollow barrel, said second barrel having a first slanted end including first skin gripping means, said second barrel in telescopic relation with said first barrel and being retractable between extended and retracted positions with respect to said first barrel; and
   spring means contacting said first and second hollow barrels for biasing said second hollow barrel toward said extended position, wherein a subcutaneous tent is formed by said first skin gripping means when said second barrel moves from said extended position to said retracted position, whereby a hypodermic needle is inserted into the subcutaneous tent during movement from said extended position to said retracted position and,
   wherein said first skin gripping means comprises a stair-like construction on said first slanted end.

5. A front syringe attachment comprising;
   a first hollow barrel mountable on a cylinder syringe, said first barrel having a first slanted end including first skin gripping means;
   a second hollow barrel, said second barrel having a second slanted end including second skin gripping means, said second barrel in telescopic relation with said first barrel and being retractable between extended and retracted positions with respect to said first barrel; and
   spring means contacting said first and second hollow barrels for biasing said second hollow barrel toward said extended position, wherein a subcutaneous tent is formed by said second skin gripping means when said second barrel moves from said extended position to said retracted position, whereby a hypodermic needle is inserted into the subcutaneous tent during movement from said extended position to said retracted position and,
   wherein said first skin gripping means comprises a stair-like construction on said first slanted end and
   wherein said second skin gripping means comprises a stair-like construction on said second slanted end.

* * * * *